United States Patent
Brünjes et al.

(10) Patent No.: US 10,479,768 B2
(45) Date of Patent: Nov. 19, 2019

(54) PROCESS FOR THE PREPARATION OF AMPHIPHILIC IMIDAZOLINIUM COMPOUNDS

(71) Applicant: BAYER ANIMAL HEALTH GMBH, Leverkusen (DE)

(72) Inventors: Marco Brünjes, Hattersheim am Main (DE); Mark James Ford, Wiesbaden-Breckenheim (DE)

(73) Assignee: Bayer Animal Health GmbH, Leverkusen (DE)

( * ) Notice: Subject to any disclaimer, the term of this patent is extended or adjusted under 35 U.S.C. 154(b) by 88 days.

(21) Appl. No.: 15/571,650

(22) PCT Filed: May 3, 2016

(86) PCT No.: PCT/EP2016/059823
§ 371 (c)(1),
(2) Date: Nov. 3, 2017

(87) PCT Pub. No.: WO2016/177693
PCT Pub. Date: Nov. 10, 2016

(65) Prior Publication Data
US 2018/0148415 A1    May 31, 2018

Related U.S. Application Data

(60) Provisional application No. 62/156,677, filed on May 4, 2015.

(51) Int. Cl.
*C07D 233/14* (2006.01)
(52) U.S. Cl.
CPC .................. *C07D 233/14* (2013.01)

(58) Field of Classification Search
CPC .................................................... C07D 233/14
See application file for complete search history.

(56) References Cited

U.S. PATENT DOCUMENTS

| | | | |
|---|---|---|---|
| 5,705,655 A | 1/1998 | Heath et al. | |
| 5,830,878 A | 11/1998 | Gorman et al. | |
| 8,044,215 B2 | 10/2011 | Yu et al. | |
| 2010/0280248 A1 | 11/2010 | Kempf | |
| 2010/0280258 A1* | 11/2010 | Yu ........................ | C07D 233/60 548/352.1 |

OTHER PUBLICATIONS

International Search Report of International Patent Application No. PCT/EP216/059823 dated Jul. 14, 2016.
Zhi, et al., "The Headgroup Evolution of Cationic Lipids for Gene Delivery," Bioconjugate Chemistry, (2013), vol. 24: 487-519.
Solodin, et al., "A Novel Series of Amphiphilic Imidazolinium Compounds for in Vitro and in Vivo Gene Delivery," Biochemistry, (1995), vol. 34: 13537-13544.

* cited by examiner

*Primary Examiner* — Matthew P Coughlin
(74) *Attorney, Agent, or Firm* — McBee Moore Woodward & Vanik IP, LLC

(57) ABSTRACT

The present invention generally relates to improved processes for the preparation of amphiphilic imidazolinium compounds such as 1-[2-(9(Z)-octadecenoyloxy)ethyl]-2-(8(Z)-heptadecenyl)-3-(2-hydroxyethyl)imidazolinium chloride (DOTIM). In particular, the invention relates to processes for the synthesis of such compounds that avoid the need for toxic reagents, are more economical, and result in less waste than conventional methods. DOTIM and similar compounds can be formulated as cationic liposomes, which are useful as chemical vectors for nucleic acid delivery in gene therapy.

25 Claims, No Drawings

PROCESS FOR THE PREPARATION OF AMPHIPHILIC IMIDAZOLINIUM COMPOUNDS

CROSS-REFERENCE TO RELATED APPLICATIONS

This application is a National Stage entry of International Application No. PCT/EP2016/059823, filed 03 May 2016, which claims priority to U.S. Provisional Application No. 62/156,677, filed 04 May 2015.

FIELD OF THE INVENTION

The present invention generally relates to improved processes for the preparation of amphiphilic imidazolinium compounds, such as 1-[2-(9(Z)-octadecenoyloxy)ethyl]-2-(8(Z)-heptadecenyl)-3-(2-hydroxyethyl)imidazolinium chloride (DOTIM). DOTIM and similar compounds can be formulated as cationic liposomes, which are useful as chemical vectors for nucleic acid delivery in gene therapy.

BACKGROUND OF THE INVENTION

Gene therapy uses nucleic acids as treatment for genetic deficiencies and a large variety of acquired diseases and includes large DNA molecules (plasmid DNA; pDNA) but also small DNA (oligonucleotides; ODN) and RNA (ribozymes, SiRNA and mRNA) molecules. The success of gene therapy is largely dependent on the development of the gene delivery vector, which can be a viral vector or nonviral vector, such as a chemical carrier or delivery of naked DNA by physical methods. Nonviral vectors have many advantages over viral ones, including simple large-scale production, lack of immunogenicity, and low toxicity.

Cationic lipids capable of forming positively-charged liposomes are one of the most widely used nonviral vectors for gene delivery (Zhi et al., Bioconjugate Chemistry, 2013, 24: 478-519). Cationic lipids are amphiphilic molecules and generally consist of a hydrophobic domain (e.g., aliphatic chains, steroid rings), a hydrophilic headgroup (e.g., amines, quaternary ammonium salts, guanidiniums, heterocycles), and a linker group (e.g., ether, ester, carbamate or amide bond) connecting the two domains. The hydrophilic headgroup enables the condensation of nucleic acids by electrostatic interactions with the negatively-charged phosphate groups of the genes, and further governs transfection efficiency. Cationic lipids are usually formulated as cationic liposomes with a neutral co-lipid like dioleoyl phosphatidyl ethanolamine (DOPE) or cholesterol to improve transfection. When mixed with negatively-charged DNA, the positively-charged liposomes spontaneously form uniquely compacted structures called lipoplexes.

Solodin and co-workers reported the utilization of imidazolinium cationic lipids as synthetic carriers to deliver genes into cells (Solodin et al., Biochemistry, 1995, 34(41): 13537-13544). These lipids included 1-[2-(9(Z)-octadecenoyloxy)ethyl]-2-(8(Z)-heptadecenyl)-3-(2-hydroxyethyl)imidazolinium chloride (DOTIM), and its analogues 1-[2-(hexadecanoyloxy)ethyl]-2-pentadecyl-3-(2-hydroxyethyl)imidazolinium chloride (DPTIM) and 1-[2-(tetradecanoyloxy)ethyl]-2-tridecyl-3-(2-hydroxyethyl)-imidazolinium chloride (DMTIM). DOTIM was found to be the most effective among the three compounds for both in vitro transfection and for in vivo gene delivery. The structures of DMTIM, DPTIM, and DOTIM are as follows:

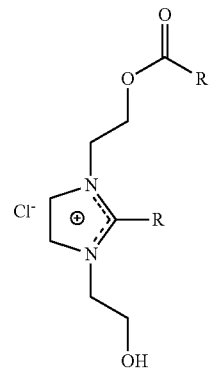

DMTIM R = —(CH$_2$)$_{12}$CH$_3$
DPTIM R = —(CH$_2$)$_{14}$CH$_3$
DOTIM R = —(CH$_2$)$_7$CH═CH(CH$_2$)$_7$CH$_3$

Methods for the preparation of aliphatic imidazolinium compounds starting with the multifunctional compound N,N'-bis(2-hydroxyethyl)ethylenediamine have been described in U.S. Pat. No. 5,705,655 (Heath), U.S. Pat. No. 5,830,878 (Gorman), and U.S. Pat. No. 8,044,215 (Yu). However, these prior processes exhibit various disadvantages. For example, in order to acylate the primary hydroxyl groups without concomitant acylation of the more nucleophilic secondary amines, the latter are protected with tert-butyloxycarbonyl groups. These protecting groups are commonly and herein referred to as "BOC" groups. This step requires the reagent di-tert-butyl dicarbonate, which is an expensive and toxic compound. Also, the BOC protecting groups have to be removed by acid hydrolysis in a subsequent step, which results in an additional amount of organic and aqueous waste.

Further, the acylation procedures of this BOC protected intermediate require the use of acid halides in the presence of base (e.g., triethylamine), or reaction with a carboxylic acid in the presence of N,N'-dicyclohexylcarbodiimide (DCC) and 4-dimethylaminopyridine (DMAP). The need for triethylamine or DMAP in the acylation reactions results in additional costs and waste. Further, the DCC/DMAP procedure results in formation of dicyclohexylurea (DCU) as a side product, and usually requires purification of the formed ester that may be labor-intensive.

There exists a need, therefore, for improved methods for preparing and purifying DOTIM and other amphiphilic imidazolinium compounds. In particular, there exists a need for such processes that are readily scalable, cost-effective, environmentally friendly, and capable of consistently yielding highly pure compounds.

SUMMARY OF THE INVENTION

Briefly, therefore, the present invention relates to improved processes for the preparation of amphiphilic imidazolinium compounds, including 1-[2-(9(Z)-octadecenoyloxy)ethyl]-2-(8(Z)-heptadecenyl)-3-(2-hydroxyethyl)imidazolinium chloride (DOTIM).

In various embodiments, the present invention is directed to a process for preparing a amphiphilic imidazolinium compound of Formula (I)

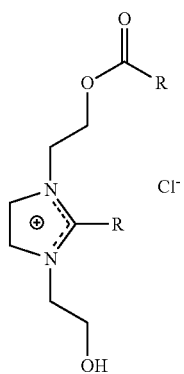

(I)

wherein R is a straight-chain, aliphatic, saturated or unsaturated hydrocarbyl group of 11 to 29 carbon atoms. The process comprises reacting a compound of Formula (II) with a hydrogen halide (HX) to provide a compound of Formula (III), wherein X is Cl, Br, or I.

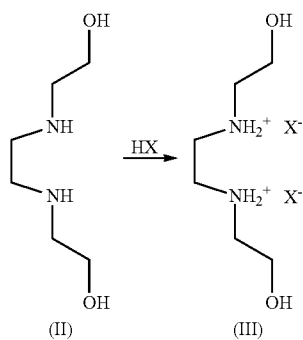

The compound of Formula (III) is reacted with a carboxylic acid halide [RC(O)Y], wherein Y is selected from the group consisting of Cl, Br, F, and I, or a carboxylic acid anhydride [RC(O)OC(O)R$^2$], wherein R is as defined above for Formula (I) and R$^2$ is a straight-chain or branched, aliphatic, saturated or unsaturated hydrocarbyl group of 1 to 29 carbon atoms, to provide a compound of Formula (IV).

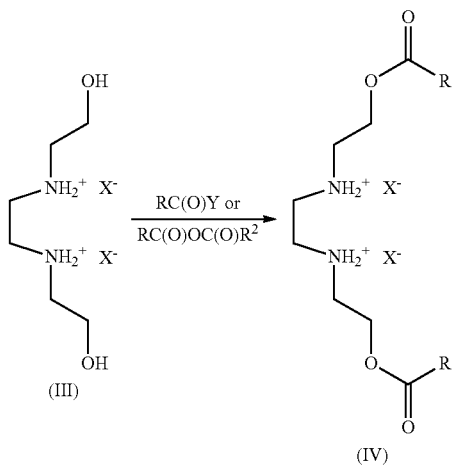

The compound of Formula (IV) is heated to provide a compound of Formula (I).

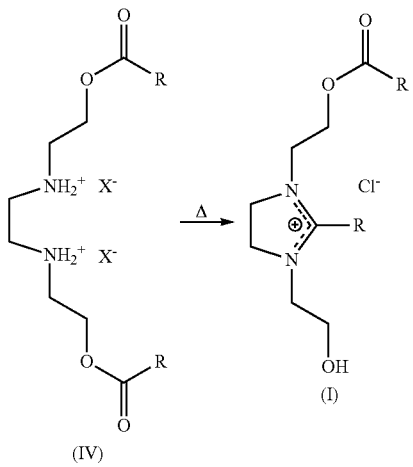

In various other embodiments, the present invention is directed to a process for preparing a compound of Formula (I)

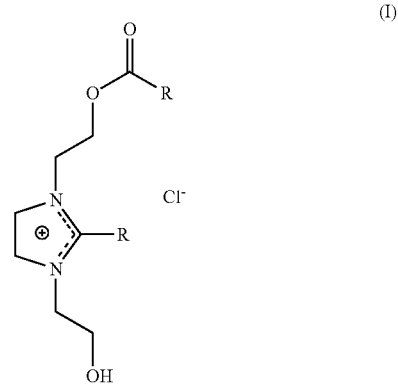

(I)

wherein R is a straight-chain, aliphatic, saturated or unsaturated hydrocarbyl group of 11 to 29 carbon atoms. The process comprises heating a compound of Formula (IV) in a reaction mixture comprising an organic solvent and a base to provide the compound of Formula (I), wherein R is as defined above and X is Cl, Br, or I.

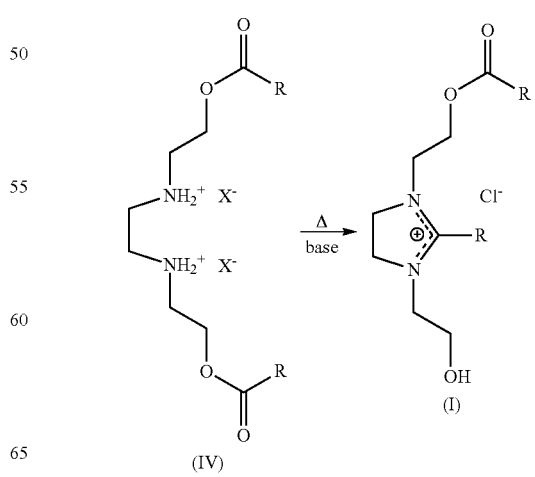

DETAILED DESCRIPTION OF THE PREFERRED EMBODIMENTS

The present invention generally relates to processes for the preparation of amphiphilic imidazolinium compounds that provide advantages over the prior art. For example, the processes avoid the use of BOC protecting groups and the need for a base during the acylation procedure, thereby reducing the cost of the process, toxicity concerns and the amount of waste generated.

In particular, the present invention provides processes for preparation of amphiphilic imidazolinium compounds of Formula (I):

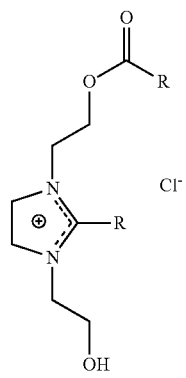
(I)

wherein R is a straight-chain, aliphatic, saturated or unsaturated hydrocarbyl group of 11 to 29 carbon atoms, or 12 to 25 carbon atoms. When unsaturated, the R group may have one or more ethylenically unsaturated linkages.

Illustrative R groups together with the carbonyl group to which it is attached (i.e., RC(O)—) include oleoyl, lauroyl, myristoyl, palmitoyl, stearoyl, linoleoyl, eicosanoyl, tricosanoyl and nonacosanoyl (derived from the fatty acids of the corresponding name: oleic, lauric, myristic, etc.). When given system names for the R groups alone, the corresponding names of the hydrocarbyl group derived from oleic acid is cis-8-heptadecenyl; from lauric acid is undecyl; from myristic acid is tridecyl; from palmitic acid is pentadecyl; from stearic acid is heptadecyl; from linoleic acid is cis,cis-8,11-heptadecydienyl; from eicosanoic acid is nonadecyl; from tricosanoic acid is dicosanyl; and from triacontanoic acid is nonacosanyl. A particularly preferred compound of Formula (I) is 1-[2-(9(Z)-octadecenoyloxyethyl]-2-[8(Z)-heptadecenyl]-3-hydroxyethylimidazolinium chloride (DOTIM):

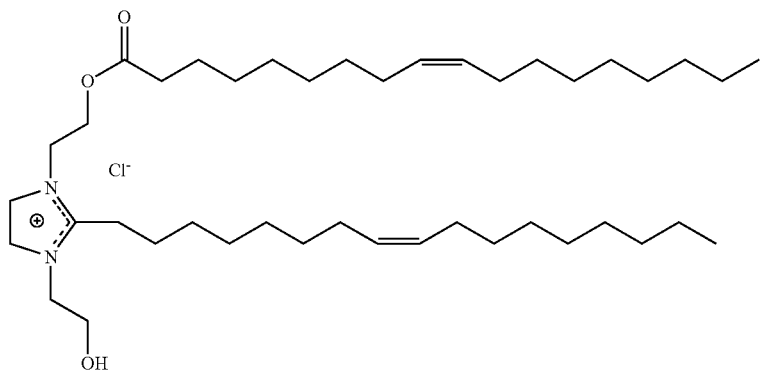

The imidazolinium compounds of the present invention are salts that have a pharmaceutically acceptable anion. Typically, the imidazolinium salt formed according to the present processes is a chloride salt. However, the anion may be exchanged to give a salt with a different anion. For example, the imidizolinium chloride salt can be dissolved in a suitable solvent and washed with a solution containing the desired anion. Although chloride is the preferred anion, also acceptable are bromide and other physiologically acceptable anions including acetate, succinate, and citrate.

In accordance with the present invention, the general process for preparing an amphiphilic imidazolinium compound of Formula (I) is as follows:

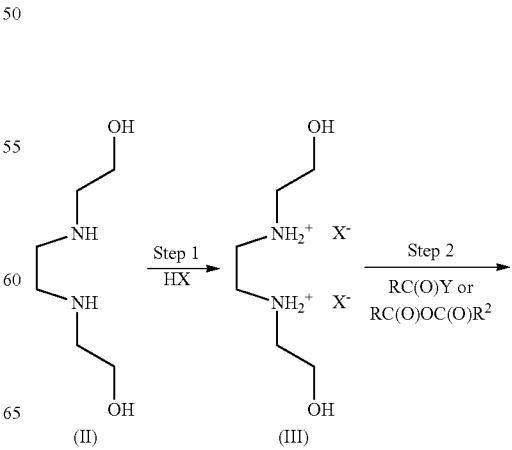

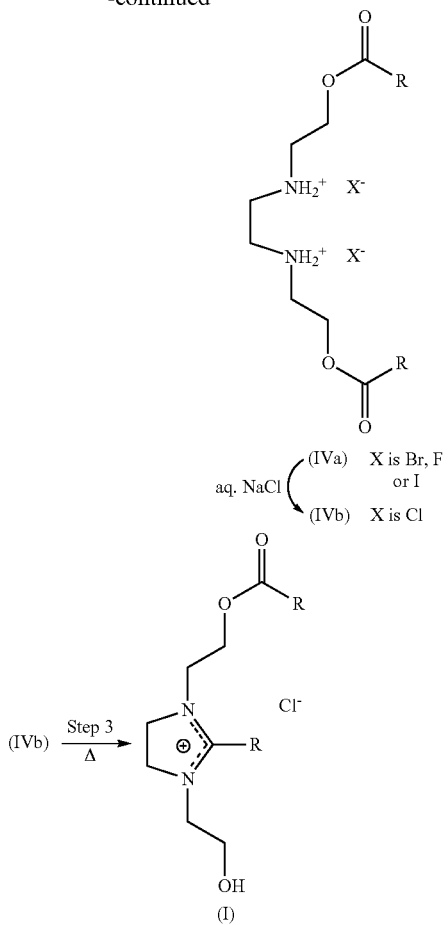

Formulas (IVa) and Formula (IVb) set forth above as the product of Step 2 are generally referred to herein (including in the appended claims) as Formula (IV).

Step 1: Protection of the Secondary Amino Groups

The first step in the process is preparation of a hydrohalide salt of N,N'-bis(2-hydroxyethyl)ethylenediamine (Formula (III)). This is achieved by reacting N,N'-bis(2-hydroxyethyl) ethylenediamine (Formula (II)) with a hydrogen halide (HX) in a reaction mixture, typically including a suitable solvent, wherein X is Cl, Br, or I. In various preferred embodiments, the hydrogen halide is hydrogen chloride (where X is Cl) or hydrogen bromide (where X is Br). In various particularly preferred embodiments, the hydrogen halide is hydrogen bromide. Generally, the hydrogen halide is introduced into a reaction mixture comprising N,N'-bis(2-hydroxyethyl)ethylenediamine. This can be accomplished, for example, by introducing hydrogen halide as a gas into the reaction mixture, which is typically in the form of a solution of the N,N'-bis(2-hydroxyethyl)ethylenediamine dissolved in an organic solvent. Alternatively, a solution of the hydrogen halide in an organic solvent (e.g. non-aqueous HBr in acetic acid, or HCl solution in methanol, ethanol, dioxane, or diethyl ether) may be added to the reaction mixture. Introducing the hydrogen halide into the reaction mixture in the liquid phase is generally preferred.

Suitable organic solvents for preparation of the hydrohalide salt of Formula (III) include, but are not limited to, $C_2$-$C_6$ carboxylic acids; $C_2$-$C_6$ nitriles; $C_1$-$C_6$ alcohols; $C_2$-$C_{10}$ ethers; $C_3$-$C_6$ alkyl acetates; $C_3$-$C_{10}$ ketones; $C_5$-$C_8$ aliphatic hydrocarbons; $C_1$-$C_6$ chlorinated hydrocarbons; $C_3$-$C_8$ alkyl carbonates; sulfolane; dimethyl sulfoxide; toluene; chlorobenzene; as well as mono- or polyphasic mixtures thereof.

Specific examples of such solvents include, but are not limited to, acetic acid, propionic acid, acetonitrile, propionitrile, methanol, ethanol, isopropanol, tert-butanol, diethyl ether, tetrahydrofuran, dioxane, methyl tert-butyl ether, 1,2-dimethoxyethane, methyl acetate, ethyl acetate, tert-butyl acetate, acetone, methyl ethyl ketone, hexane, heptane, cyclohexane, dichloromethane, chloroform, 1,2-dichloroethane, propylene carbonate, sulfolane, dimethyl sulfoxide, toluene, chlorobenzene, and combinations thereof. Preferably, the solvent is selected from the group consisting of acetic acid, methanol, ethanol, isopropanol, ethyl acetate, and combinations thereof.

The reaction to form the hydrohalide salt of Formula (III) is typically conducted at a temperature of from about 0° C. to about 60° C., and more typically at a temperature of from about 10° C. to about 30° C., for example, by controlled addition of the hydrogen halide to the reaction mixture.

Typically, the starting material is converted to a hydrohalide salt of Formula (III) during a reaction time of from about 10 to about 120 minutes, and more typically from about 30 to about 60 minutes following reagent addition.

The compound of Formula (III), in the form a hydrohalide salt, readily forms a precipitate in the reaction mixture and can be isolated by filtration. The recovered product is typically then washed and dried under vacuum.

Step 2: Acylation of the Primary Hydroxyl Groups

With the secondary amino groups of N,N'-bis(2-hydroxyethyl)ethylenediamine protected as the halide salt, the primary hydroxyl groups of the compound of Formula (III) are acylated to produce the diester.

The acylating agent can be an activated carboxylic acid derivative such as a carboxylic acid halide (RC(O)Y) or carboxylic acid anhydride (RC(O)OC(O)R²), where R is as defined above for Formula (I) and R² is a straight-chain or branched, aliphatic, saturated or unsaturated hydrocarbyl group of 1 to 29 carbon atoms, or 12 to 25 carbon atoms. In the carboxylic acid anhydride, R and R² may the same (i.e., a symmetric carboxylic acid anhydride). However, R and R² are typically not the same. Typically, R² is a $C_1$-$C_{10}$ straight-chain or branched aliphatic hydrocarbon, and more typically R² is a $C_3$-$C_{10}$ branched aliphatic hydrocarbon. It is currently believed that sterically hindered or branched R² groups (e.g., tert-butyl or isopropyl) lead to the desired product while minimizing formation of undesired mixed product esters. In the carboxylic acid halide, Y is typically selected from the group consisting of Cl, Br, F, and I. More typically, Y is Cl or Br. Y can be identical to the counterion, X, of the compound of Formula (III), but this is not required. Carboxylic acid chlorides are generally preferred over bromides, fluorides, and iodides as well as carboxylic acid anhydrides as the acylating agent because of their lower cost and ready availability. For the preparation of DOTIM, the carboxylic acid halide is preferably oleic acid chloride.

Carboxylic acid halide acylating agents are commercially available. However, it has been discovered that higher yields of the compound of Formula (IV) may be attained when the carboxylic acid halide is prepared contemporaneously or shortly prior to its use in the process of the present invention. One suitable process for preparing a carboxylic acid halide acylating agent (oleic acid chloride) is set forth in Example 2.

For hydrobromide salts of Formula (III), reaction with a carboxylic acid bromide or carboxylic acid anhydride gives the compound of Formula (IVa) shown above. Similarly, for hydrochloride salts of Formula (III), reaction with an acid chloride or carboxylic acid anhydride gives a compound of Formula (IVb).

For the acylation step, the hydrohalide salt of N,N'-bis(2-hydroxyethyl)ethylenediamine (Formula (III)) is diluted in an organic solvent followed by addition of the activated carboxylic acid acylating agent. Suitable organic solvents for the acylation step include, but are not limited to, $C_2$-$C_6$ nitriles; $C_2$-$C_{10}$ ethers; $C_3$-$C_6$ alkyl acetates; $C_3$-$C_{10}$ ketones; $C_5$-$C_8$ aliphatic hydrocarbons; $C_1$-$C_6$ chlorinated hydrocarbons; $C_3$-$C_8$ alkyl carbonates; sulfolane; dimethyl sulfoxide; toluene; chlorobenzene; as well as the mono- or polyphasic mixtures thereof.

Specific examples of such solvents include, but are not limited to, acetonitrile, propionitrile, diethyl ether, tetrahydrofuran, dioxane, methyl tert-butyl ether, 1,2-dimethoxyethane, methyl acetate, ethyl acetate, tert-butyl acetate, acetone, methyl ethyl ketone, hexane, heptane, cyclohexane, dichloromethane, chloroform, 1,2-dichloroethane, propylene carbonate, sulfolane, dimethyl sulfoxide, toluene, and chlorobenzene. Preferably, the solvent is selected from acetonitrile, propionitrile, dichloromethane, chloroform, tetrahydrofuran, and combinations thereof.

The acylation is typically conducted at a temperature from about 0° C. to about 120° C., more typically from about 20° C. to about 100° C. and, still more typically, from about 40° C. to about 80° C.

The acylation reaction is typically conducted over a time period of from about 1 to about 12 hours, more typically from about 2 to about 6 hours.

When the acylating agent is a carboxylic acid halide, hydrogen halide gas is evolved during the course of the reaction and can be absorbed using a gas scrubber. When the acylating agent is a carboxylic acid anhydride, byproduct carboxylic acid is produced and retained in the organic solvent.

The acylation of the hydrohalide salt of N,N'-bis(2-hydroxyethyl)ethylenediamine (Formula (III)) proceeds smoothly, and provides the requisite diester of Formula (IV) in high yield. Upon completion of the reaction, the reaction mixture is typically cooled to a temperature from about 20° C. to about 40° C. and may be diluted with acetone to improve filtration of the formed precipitate. The precipitated product of Formula (IV) is then readily recovered, the filtrate washed, and the recovered solid dried under vacuum.

In contrast to acylation processes described in the prior art, no addition of base is required for this transformation. In addition, the acylating step of the present process is typically conducted in the absence of any acid catalyst. In particular, this step does not utilize acid catalysts such as p-toluene sulfonic acid, benzenesulfonic acid, sulfoacetic acid, a phosphorus acid, and phosphorus trichloride.

In various preferred embodiments, X in Formula III is Br and the hydrobromide salt of N,N'-bis(2-hydroxyethyl)ethylenediamine (Formula (III)) is reacted with a carboxylic acid halide (e.g., oleic acid chloride). This reaction has been observed to readily form a compound of Formula (IVb). Where X in Formula III is Cl, the hydrochloride salt of N,N'-bis(2-hydroxyethyl)ethylenediamine (Formula (III)) may also be reacted with a carboxylic acid halide (e.g., oleic acid chloride). Based on its solubility, however, it may be necessary to dissolve the chloride salt of N,N'-bis(2-hydroxyethyl)ethylenediamine in a highly polar solvent, such as for example, sulfolane, dimethylformamide (DMF), and dimethylacetamide (DMAC). This procedure is generally less desired due to the additional work-up required and added costs.

Conversion of Hydrohalide Salt IVa to Hydrochloride Salt IVb

Since chloride is the counterion in the final product of Formula (I), an additional washing step is needed where the compound of Formula (IV) is a hydrohalide salt other than the hydrochloride salt (e.g., where the compound of Formula (III) is reacted with a carboxylic acid halide RC(O)Y, where Y is not Cl). However, when hydrochloride salt (IVb) is prepared from a compound of Formula (III), washing is unnecessary.

For any required washing step, the compound of Formula (IVa) is dissolved in a suitable solvent and washed with a concentrated aqueous solution of sodium chloride. Often multiple washings are utilized, e.g., 2 or more washings may be utilized. This washing to effect anion exchange is usually conducted at a temperature from about 0° C. to about 60° C., more typically from about 10° C. to about 30° C. and, still more typically, from about 15° C. to about 25° C. After separating the final aqueous sodium chloride (brine) layer, the organic phase is concentrated to yield the desired hydrochloride salt of Formula (IVb).

Suitable solvents for the anion exchange step include, but are not limited to, $C_2$-$C_6$ nitriles; $C_2$-$C_{10}$ ethers; $C_3$-$C_6$ alkyl acetates; $C_3$-$C_{10}$ ketones; $C_5$-$C_8$ aliphatic hydrocarbons; $C_1$-$C_6$ chlorinated hydrocarbons; toluene; chlorobenzene; as well as the mono- or polyphasic mixtures thereof.

Specific examples of such solvents include, but are not limited to, acetonitrile, propionitrile, diethyl ether, tetrahydrofuran, dioxane, methyl tert-butyl ether, 1,2-dimethoxyethane, methyl acetate, ethyl acetate, tert-butyl acetate, acetone, methyl ethyl ketone, hexane, heptane, cyclohexane, dichloromethane, chloroform, 1,2-dichloroethane, toluene, chlorobenzene, and mixtures thereof. Preferably, the solvent is selected from dichloromethane, chloroform, 1,2-dichloroethane, methyl acetate, ethyl acetate, toluene, and combinations thereof.

Step 3: Rearrangement Reaction

To effect the rearrangement reaction, the compound of Formula (IVb) is dissolved in a reaction mixture comprising a suitable solvent and this reaction mixture is heated and stirred whereupon acyl group migration followed by condensation occurs, which results in formation of the imidazolinium compound of Formula (I).

Suitable solvents for the rearrangement reaction include, but are not limited to, $C_2$-$C_6$ nitriles; $C_1$-$C_6$ alcohols; $C_2$-$C_{10}$ ethers; $C_3$-$C_6$ alkyl acetates; $C_3$-$C_{10}$ ketones; $C_5$-$C_8$ aliphatic hydrocarbons; $C_1$-$C_6$ chlorinated hydrocarbons; $C_3$-$C_8$ alkyl carbonates; sulfolane; dimethyl sulfoxide; toluene; chlorobenzene; as well as the mono- or polyphasic mixtures thereof.

Specific examples of such solvents include, but are not limited to, acetonitrile, propionitrile, methanol, ethanol, isopropanol, tert-butanol, diethyl ether, tetrahydrofuran, dioxane, methyl tert-butyl ether, 1,2-dimethoxyethane, methyl acetate, ethyl acetate, tert-butyl acetate, acetone, methyl ethyl ketone, hexane, heptane, cyclohexane, dichloromethane, chloroform, 1,2-dichloroethane, propylene carbonate, sulfolane, dimethyl sulfoxide, toluene, chlorobenzene, and mixtures thereof.

In certain embodiments, the solvent is a mixture of a chlorinated hydrocarbon and an alcohol such as, for example, a mixture of chloroform and methanol. In such instances, the weight ratio of chloroform to methanol is typically from about 4:1 to about 10:1, or from about 6:1 to about 8:1. Additionally or alternatively, the volumetric ratio of chloroform to methanol is typically from about 2:1 to about 6:1, or from about 3:1 to about 5:1.

In certain embodiments, along with the solvent or solvent mixture the reaction mixture further includes a base. In some embodiments a weak base is employed. Suitable weak bases include, but are not limited to, sodium bicarbonate (sodium hydrogen carbonate), potassium bicarbonate (potassium hydrogen carbonate), potassium dihydrogen phosphate (monopotassium phosphate), dipotassium hydrogen phosphate (dipotassium phosphate), tertiary amines, and mixtures thereof.

Generally, the base is incorporated at a molar ratio to the compound of Formula (IVb) of from about 0.25:1 to about 1.75:1 or from about 0.8:1 to about 1.5:1. In certain embodiments the base is incorporated at a molar ratio to the compound of Formula (IVb) of from about 1:1 to about 1:5:1, or from about 1:1 to about 1.2:1 (e.g., about 1.1:1).

In addition to the organic solvent or solvent mixture, and optional base, a drying agent can be added to the reaction mixture prior to heating. Suitable drying agents include, for example, molecular sieves (e.g., those having a pore size of from 2 Å to 5 Å), calcium chloride, magnesium sulfate, and sodium sulfate. Particularly suitable drying agents include molecular sieves (e.g., those having a pore size of from 2 Å to 5 Å or about 3 Å) and magnesium sulfate. Activated charcoal is also a suitable drying agent. The amount of drying agent is not narrowly critical, but should be sufficient to take up the water formed during the rearrangement/condensation reaction.

The reaction mixture is typically conducted at a temperature from about 20° C. to about 100° C., more typically from about 40° C. to about 80° C. and, still more typically, from about 50° C. to about 70° C.

The rearrangement step is typically conducted over a time period of from about 2 to about 48 hours, more typically from about 12 to about 36 hours. Although such time periods are acceptable, in certain embodiments where a base is incorporated into the reaction mixture, the rearrangement reaction proceeds at a faster rate. In such embodiments the rearrangement step is conducted over a time period of from about 2 to about 12 hours, or from about 4 to about 10 hours, or even about 5 hours or about 6 hours.

After the reaction mixture is cooled or allowed to cool to room temperature, the mixture is filtered to remove a solids fraction and provide a filtrate containing the imidazolinium compound of Formula (I). The filtrate is concentrated to yield a crude product typically in the form of a waxy solid. The crude product can be purified by suitable methods known in the art including, for example, washing with solvent, by recrystallization, or even by a suitable chromatographic method.

Preferred purification/product recovery protocols include treating the crude product filtrate with acetone, followed by filtration and concentration to recover the desired solid product. Another preferred purification/product recovery protocol involves filtration utilizing a silica column and dichloromethane or chloroform. Notably, these preferred product purification/product recovery protocol are not chromatographic methods and therefore much simpler and more suitable for use at commercial scale than chromatography-based recovery methods conventionally used in the art. Advantageously, purification/product recovery protocols used in the present methods that are not chromatographic provide product purities in excess of 95% or higher (e.g., in excess of 97%).

Generally, the rearrangement step provides the compound of Formula (I) at a yield (based on the compound of Formula (IVb)) of at least about 70%, at least about 75%, at least about 80%, at least about 85%, at least about 90%, or at least about 95% (e.g., about 97% or higher).

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis of
N,N'-bis(2-hydroxyethyl)ethane-1,2-diaminium dibromide

N,N'-Bis(2-hydroxyethyl)ethylenediamine (20 g, 0.135 mol) was dissolved in 100 ml acetic acid (exothermic). After cooling this solution to approximately 20° C., hydrobromic acid (0.283 mol; 50.3 mL, 33% solution in acetic acid) was slowly added to the reaction mixture over the course of 45 minutes, so that the temperature of the reaction mixture did not exceed 30° C. A white precipitate formed during the addition of hydrobromic acid to the reaction mixture. After complete addition, the reaction mixture was stirred for 30 minutes, followed by filtration of the precipitate. The precipitate was then washed with acetonitrile (2×25 mL) and dried at 30° C. under vacuum (5 mbar) to give 40.58 g (0.131 mol, 97% yield) of N,N'-bis(2-hydroxyethyl)ethane-1,2-diaminium dibromide as a white solid. The structure of the product was confirmed by NMR spectroscopy: $^1$H-NMR (DMSO-$d_6$, 400 MHz) δ=8.62 (4H, bs), 5.34 (2H, bs), 3.67 (4H, bs), 3.29 (4H, bs), and 3.07 (4H, bs) ppm.

Example 2

Synthesis of N,N'-bis{2-[(9Z)-octadec-9-enoyloxy]ethyl}ethane-1,2-diaminium dibromide N,N'-bis{2-[(9Z)-octadec-9-enoyloxy]ethyl}ethane-1,2-diaminium dibromide was prepared by acylating N,N'-Bis(2-hydroxyethyl)ethane-1,2-diaminium dibromide with freshly prepared oleic acid chloride.

Oleic acid chloride was prepared by dissolving oleic acid (9.0 g, 0.0319 mol, 99% purity) in 20 mL dichloromethane, followed by addition of oxalyl chloride (8.08 g, 0.064 mol) at 20° C. After addition, the reaction mixture was stirred for 60 minutes. Dichloromethane and excess oxalyl chloride was evaporated at 30° C. under vacuum (750 mbar, gradually to 50 mbar) to give 9.5 g (0.0315 mol, 99% yield) of oleic acid chloride as a colorless oil. The structure of the product was confirmed by NMR spectroscopy: $^1$H-NMR (CDCl$^3$, 400 MHz) δ=5.34 (2H, m), 2.88 (2H, t), 2.01 (4H, m), 1.71 (2H, m), 1.31 (20H, m), and 0.88 (3H, t) ppm.

N,N'-Bis(2-hydroxyethyl)ethane-1,2-diaminium dibromide (25 g, 0.0806 mol) prepared as described in Example 1 was added at 20° C. into 200 mL of acetonitrile to provide a white slurry. After heating to approximately 82° C., freshly prepared oleic acid chloride (72.8 g, 0.242 mol) was added to the reaction mixture over 1 hour, followed by further stirring at approximately 82° C. for 3 hours. During that time, gaseous hydrogen chloride evolved from the reaction mixture, which was absorbed in a gas scrubber. After cooling to 40° C., the reaction mixture was diluted with 150 mL acetone to improve filtration behavior of the formed precipitate. At 20° C., the slurry was filtered and consecutively washed with acetone (1×20 mL), water (1×40 mL) and acetone (2×25 mL). The remaining solid was dried at 40° C. under vacuum (5 mbar) to give 54.1 g (0.0645 mol, 80% yield) of N,N'-bis{2-[(9Z)-octadec-9-enoyloxy]ethyl}ethane-1,2-diaminium dibromide as an off-white solid. The bromide/chloride ratio in the product was found to be 18:1, as determined by ion chromatography. The structure of the product was confirmed by NMR spectroscopy: $^1$H-NMR (CDCl$_3$, 400 MHz) δ=9.50 (4H, bs), 5.34 (4H, m), 4.52 (4H, m), 3.81 (4H, bs), 3.45 (4H, bs), 2.47 (4H, m), 2.00 (8H, m), 1.62 (4H, m), 1.29 (40H, m), and 0.88 (6H, m) ppm.

Example 3

Synthesis of N,N'-bis{2-[(9Z)-octadec-9-enoyloxy]ethyl}ethane-1,2-diaminium dichloride N,N'-Bis{2-[(9Z)-octadec-9-enoyloxy]ethyl}ethane-1,2-diaminium dibromide (42 g, 0.050 mol) was dissolved in chloroform (500 mL). To this solution at 20° C. were added 250 mL of water and 500 mL of concentrated aqueous sodium chloride solution. The reaction mixture was agitated by stirring for one hour, and then the organic phase separated from the aqueous layer. Prior centrifugation (at 3000 to 5000 RPM) of the reaction mixture typically gave better phase separation. The organic layer was treated again (2×) with aqueous sodium chloride solution in the same manner Finally, the organic layer was washed with water, dried over 2 g of calcium chloride, and concentrated at 40° C. under vacuum (500 mbar, gradually to 20 mbar) to yield 31.9 g (0.0425 mol, 85%) of N,N'-bis{2-[(9Z)-octadec-9-enoyloxy]ethyl}ethane-1,2-diaminium dichloride as an off-white solid. The structure of the product was confirmed by NMR spectroscopy: $^1$H-NMR (CDCl3, 400 MHz) δ=10.10 (4H, bs), 5.35 (4H, m), 4.49 (4H, m), 3.69 (4H, bs), 3.38 (4H, m), 2.45 (4H, m), 1.99 (8H, m), 1.61 (4H, m), 1.29 (40H, m), and 0.88 (6H, m) ppm.

The bromide/chloride ratio of the product obtained after the 3rd washing with concentrated aqueous sodium chloride solution was found to be 1:180.

Example 4

Synthesis of 1-[2-(9(Z)-octadecenoyloxy)ethyl]-2-(8(Z)-heptadecenyl)-3-(2-hydroxyethyl)imidazolinium chloride N,N'-Bis{2-[(9Z)-octadec-9-enoyloxy]ethyl}ethane-1,2-diaminium dichloride (20 g, 0.0266 mol) was dissolved in a mixture of chloroform (160 mL) and methanol (40 mL), then to this mixture was added 3 Å molecular sieves (5 g). The reaction mixture was heated to approximately 54° C. and stirred for 24 hours. The reaction mixture was then cooled to room temperature and filtered to remove solids. The filtrate was concentrated in vacuum (500 mbar, gradually to 5 mbar) at 40° C. to give a yellowish waxy solid. The crude product was treated with 30 mL of acetone and stirred for 30 minutes at 40° C. The resulting slurry was filtered, and the filtrate concentrated again under vacuum to give 14.4 g (0.0207 mol, 78% yield) of 1-[2-(9(Z)-octadecenoyloxy)ethyl]-2-(8(Z)-heptadecenyl)-3-(2-hydroxyethyl)imidazolinium chloride as a colorless, waxy solid. The structure of the product was confirmed by NMR spectroscopy: $^1$H-NMR (CDCl$_3$, 400 MHz) δ=6.12 (1H, bs), 5.34 (4H, m), 4.34 (2H, m), 4.09 (4H, s), 3.87 (2H, m), 3.77 (2H, m), 3.52 (2H, m), 2.78 (2H, m), 2.32 (2H, m), 2.00 (8H, m), 1.59 (4H, m), 1.30 (40H, m), and 0.88 (6H, m) ppm.

Example 5

Synthesis of (1-[2-(9(Z)-octadecenoyloxy)ethyl]-2-(8(Z)-heptadecenyl)-3-(2-hydroxyethyl)imidazoliniumchloride) with base addition N,N'-bis{2-[(9Z)-octadec-5-enoyloxy]ethyl}ethan-1,2-diaminiumdichloride (140 g, 0.186 mol) and sodium bicarbonate (sodium hydrogen carbonate) (15.68 g, 0.205 mol) were suspended in a mixture of chloroform (1120 ml) and methanol (280 ml) at 20° C. The reaction mixture was heated to a temperature of approximately 50-52° C. and stirred for 5 hrs. The mixture was then concentrated in vacuum (40° C.; 150 mbar) to remove the solvents and provide a residue (196 g). The crude product residue was dissolved in acetone (1120 ml) and active charcoal (28 g, having been dried at 120° C.) was then added and the suspension stirred for 30 minutes at room temperature. The resulting slurry was filtered, and the filter cake was washed with acetone (150 ml). The combined clear yellow filtrate was concentrated under vacuum (40° C.; 4 mbar) to provide 120.3 g (0.173 mol, 92.7% yield) of (1-[2-(9(Z)-octadecenoyloxy)ethyl]-2-(8(Z)-heptadecenyl)-3-(2-hydroxyethyl)imidazoliniumchloride).

Embodiments

For further illustration, additional non-limiting embodiments of the present disclosure are set forth below.

Embodiment A1 is a process for preparing a compound of Formula (I)

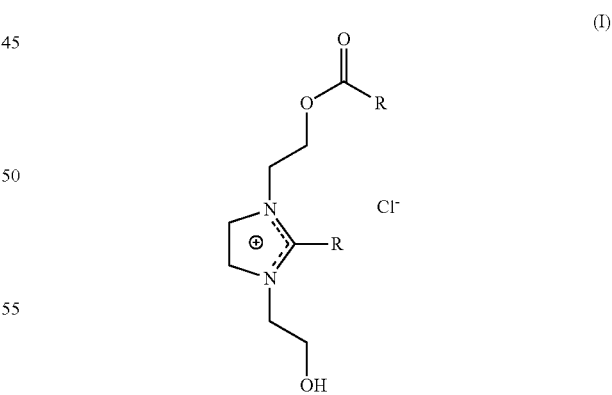

wherein R is a straight-chain, aliphatic, saturated or unsaturated hydrocarbyl group of 11 to 29 carbon atoms, the process comprising: reacting a compound of Formula (II) with a hydrogen halide (HX) to provide a compound of Formula (III), wherein X is Cl, Br, or I;

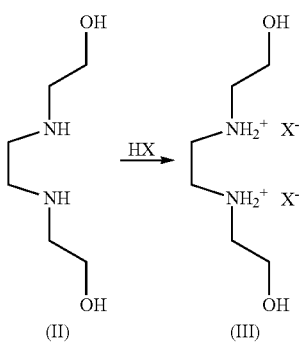

reacting a compound of Formula (III) with a carboxylic acid halide [RC(O)Y], wherein Y is selected from the group consisting of Cl, Br, F, and I, or a carboxylic acid anhydride [RC(O)OC(O)R$^2$], wherein R is as defined above for Formula (I) and R$^2$ is a straight-chain or branched, aliphatic, saturated or unsaturated hydrocarbyl group of 1 to 29 carbon atoms, to provide a compound of Formula (IV); and

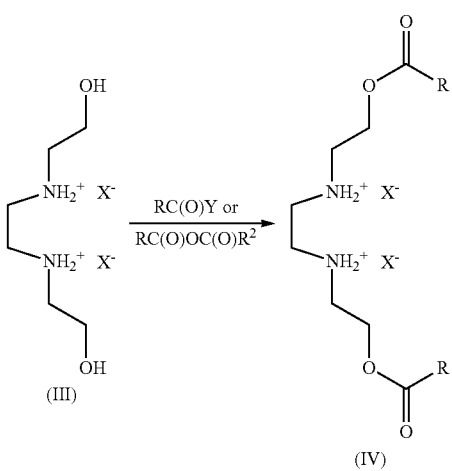

heating the compound of Formula (IV) to provide a compound of Formula (I)

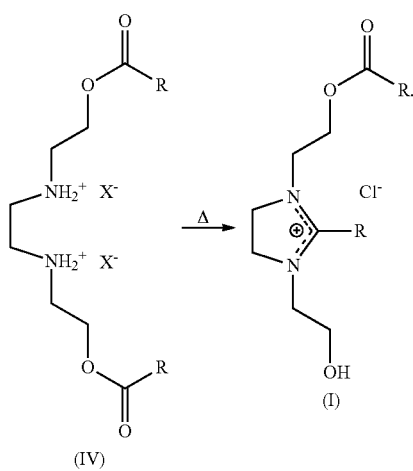

Embodiment A2 is the process of embodiment A1, wherein when the compound of Formula (III) is reacted with a carboxylic acid halide [RC(O)Y], and X is not Cl and a compound of Formula (IVa) is provided, the process further comprising washing the compound of Formula (IVa) with an aqueous solution of sodium chloride to provide a compound of Formula (IVb)

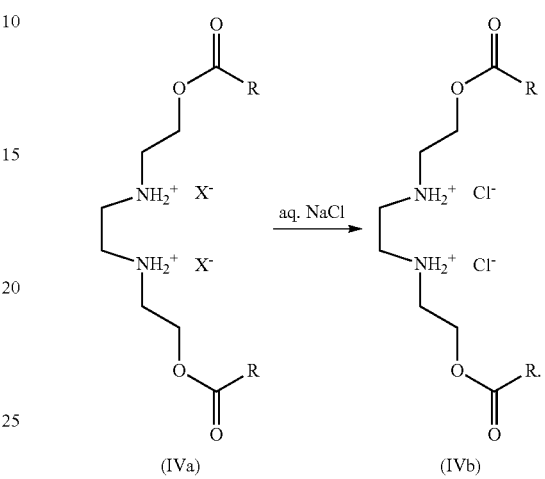

Embodiment A3 is the process of embodiment A1, wherein when the compound of Formula (III) is reacted with a carboxylic acid anhydride [RC(O)OC(O)R$^2$], or a carboxylic acid halide [RC(O)Y] and X=Cl and a compound of Formula (IVb) is provided.

Embodiment A4 is the process of embodiment A2 or A3, wherein the compound of Formula (III) is reacted with a carboxylic acid halide or carboxylic acid anhydride in the absence of an acid catalyst.

Embodiment A5 is the process of embodiment A2 or A3, wherein the compound of Formula (III) is reacted with a carboxylic acid halide or carboxylic acid anhydride in the absence of an acid catalyst selected from the group consisting of p-toluene sulfonic acid, benzenesulfonic acid, sulfoacetic acid, a phosphorus acid, and phosphorus trichloride.

Embodiment A6 is the process of any of embodiments A1 to A5, wherein the compound of Formula (II) is reacted with the hydrogen halide (HX) in a reaction mixture further comprising an organic solvent.

Embodiment A7 is the process of embodiment A6, wherein the organic solvent is selected from C$_2$-C$_6$ carboxylic acids, C$_2$-C$_6$ nitriles, C$_1$-C$_6$ alcohols, C$_2$-C$_{10}$ ethers, C$_3$-C$_6$ alkyl acetates, C$_3$-C$_{10}$ ketones, C$_5$-C$_8$ aliphatic hydrocarbons, C$_1$-C$_6$ chlorinated hydrocarbons, C$_3$-C$_8$ alkyl carbonates, sulfolane, dimethyl sulfoxide, toluene, chlorobenzene and combinations thereof.

Embodiment A8 is the process of embodiment A7, wherein the organic solvent is selected from the group consisting of acetic acid, propionic acid, acetonitrile, propionitrile, methanol, ethanol, isopropanol, tert-butanol, diethyl ether, tetrahydrofuran, dioxane, methyl-tert-butyl ether, dimethoxyethane, methyl acetate, ethyl acetate, tert-butyl acetate, acetone, methyl ethyl ketone, hexane, heptane, cyclohexane, dichloromethane, chloroform, dichloroethane, propylene carbonate, sulfolane, dimethyl sulfoxide, toluene, chlorobenzene and combinations thereof.

Embodiment A9 is the process of embodiment A8, wherein the organic solvent is selected from the group consisting of acetic acid, methanol, ethanol, isopropanol, ethyl acetate, and combinations thereof.

Embodiment A10 is the process of any of embodiments A1 to A9, wherein the compound of Formula (II) is reacted with a hydrogen halide at a temperature from about 0° C. to about 60° C.

Embodiment A11 is the process of embodiment A10, wherein the temperature is from about 10° C. to about 30° C.

Embodiment A12 is the process of any of embodiments A1 to A11, wherein $R^2$ is a $C_1$-$C_{10}$ straight-chain or branched aliphatic hydrocarbon.

Embodiment A13 is the process of any of embodiments A1 to A11, wherein $R^2$ is a $C_3$-$C_{10}$ branched aliphatic hydrocarbon.

Embodiment A14 is the process of any of embodiments A1 to A13, wherein the compound of Formula (III) is reacted with a carboxylic acid halide [RC(O)Y], wherein R is a $C_{11}$-$C_{29}$ straight-chain hydrocarbyl group, and Y is Cl or Br.

Embodiment A15 is the process of embodiment A14, wherein R is a $C_{12}$-$C_{25}$ straight-chain, aliphatic, saturated or unsaturated hydrocarbyl group.

Embodiment A16 is the process of embodiment A14, wherein the carboxylic acid halide is oleic acid chloride.

Embodiment A17 is the process of any of embodiments A1 to A13, wherein the compound of Formula (III) is reacted with a carboxylic acid anhydride [RC(O)C(O)$R^2$], wherein R is a $C_{11}$-$C_{29}$ straight-chain saturated or unsaturated aliphatic hydrocarbyl group and $R^2$ is a $C_1$-$C_{10}$ straight-chain or branched aliphatic hydrocarbon.

Embodiment A18 is the process of embodiment A17, wherein R is a $C_{12}$-$C_{25}$ straight-chain saturated or unsaturated hydrocarbyl group.

Embodiment A19 is the process of any of embodiments A1 to A18, wherein the compound of Formula (III) is reacted with a carboxylic acid anhydride [RC(O)OC(O)$R^2$], or a carboxylic acid halide [RC(O)Y] in a reaction mixture further comprising an organic solvent.

Embodiment A20 is the process of embodiment A19, wherein the organic solvent is selected from the group consisting of $C_2$-$C_6$ nitriles, $C_2$-$C_{10}$ ethers, $C_3$-$C_6$ alkyl acetates, $C_3$-$C_{10}$ ketones, $C_5$-$C_8$ aliphatic hydrocarbons, $C_1$-$C_6$ chlorinated hydrocarbons, $C_3$-$C_8$ alkyl carbonates, sulfolane, dimethyl sulfoxide, toluene, chlorobenzene and combinations thereof.

Embodiment A21 is the process of embodiment A20 wherein the organic solvent is selected from the group consisting of acetonitrile, propionitrile, diethyl ether, tetrahydrofuran, dioxane, methyl-tert-butyl ether, dimethoxyethane, methyl acetate, ethyl acetate, tert-butyl acetate, acetone, methyl ethyl ketone, hexane, heptane, cyclohexane, dichloromethane, chloroform, dichloroethane, propylene carbonate, sulfolane, dimethyl sulfoxide, toluene, dichlorobenzene and combinations thereof.

Embodiment A22 is the process of embodiment A21, wherein the organic solvent comprises acetonitrile, propionitrile, dichloromethane, chloroform, tetrahydrofuran, and combinations thereof.

Embodiment A23 is the process of any of embodiments A1 to A22, wherein the compound of Formula (III) is reacted with a carboxylic acid anhydride or carboxylic acid halide at a temperature from about 0° C. to about 120° C.

Embodiment A24 is the process of embodiment A23, wherein the temperature is from about 20° C. to about 120° C.

Embodiment A25 is the process of embodiment A24, wherein the temperature is from about 40° C. to about 85° C.

Embodiment A26 is the process of any of embodiments A2 to A25, wherein a compound of Formula (IVa) is contacted with an aqueous solution of sodium chloride to provide the compound of Formula (IVb).

Embodiment A27 is the process of embodiment A26, wherein the compound of Formula (IVa) is contacted with the aqueous solution of sodium chloride in a reaction mixture further comprising an organic solvent.

Embodiment A28 is the process of embodiment A27, wherein the organic solvent is selected from the group consisting of $C_2$-$C_6$ nitriles, $C_2$-$C_{10}$ ethers, $C_3$-$C_6$ alkyl acetates, $C_3$-$C_{10}$ ketones, $C_5$-$C_8$ aliphatic hydrocarbons, $C_1$-$C_6$ chlorinated hydrocarbons, toluene, chlorobenzene and combinations thereof.

Embodiment A29 is the process of embodiment A28, wherein the organic solvent is selected from the group consisting of acetonitrile, propionitrile, diethyl ether, tetrahydrofuran, dioxane, methyl-tert-butyl ether, acetone, methyl ethyl ketone, hexane, heptane, cyclohexane, dichloromethane, chloroform, dichloroethane, toluene, chlorobenzene and combinations thereof.

Embodiment A30 is the process of embodiment A29, wherein the organic solvent comprises dichloromethane, chloroform, 1,2-dichloroethane, methyl acetate, ethyl acetate, toluene, and combinations thereof.

Embodiment A31 is the process of any of embodiments A27 to A30, wherein the compound of Formula (IVa) is contacted with an aqueous solution of sodium chloride at a temperature from about 0° C. to about 60° C.

Embodiment A32 is the process of embodiment A31, wherein the temperature is from about 10° C. to about 30° C.

Embodiment A33 is the process of any of embodiments A2 to A32, wherein the compound of Formula (IVb) is heated in a reaction mixture comprising the compound of Formula (IVb) and an organic solvent.

Embodiment A34 is the process of embodiment A33, wherein the organic solvent is selected from the group consisting of $C_2$-$C_6$ nitriles, $C_1$-$C_6$ alcohols, $C_2$-$C_{10}$ ethers, $C_3$-$C_6$ alkyl acetates, $C_3$-$C_{10}$ ketones, $C_5$-$C_8$ aliphatic hydrocarbons, $C_1$-$C_6$ chlorinated hydrocarbons, $C_3$-$C_8$ alkyl carbonates, sulfolane, dimethyl sulfoxide, toluene, chlorobenzene and combinations thereof.

Embodiment A35 is the process of embodiment A34, wherein the organic solvent is selected from the group consisting of acetonitrile, propionitrile, methanol, ethanol, isopropanol, tert-butanol, diethyl ether, tetrahydrofuran, dioxane, methyl-tert-butyl ether, dimethoxyethane, methyl acetate, ethyl acetate, tert-butyl acetate, acetone, methyl ethyl ketone, hexane, heptane, cyclohexane, dichloromethane, chloroform, dichloroethane, propylene carbonate, sulfolane, dimethyl sulfoxide, toluene, chlorobenzene and combinations thereof.

Embodiment A36 is the process of embodiment A35, wherein the organic solvent comprises chloroform and methanol.

Embodiment A37 is the process of any of embodiments A33 to A36 wherein the reaction mixture comprising the compound of Formula (IVb) further comprises a base.

Embodiment A38 is the process of embodiment A37, wherein the base is a weak base.

Embodiment A39 is the process of embodiment A38, wherein the base is sodium bicarbonate, potassium bicarbonate, potassium dihydrogen phosphate, dipotassium hydrogen phosphate, a tertiary amine, or a mixture thereof.

Embodiment A40 is the process of any of embodiments A33 to A39, wherein the reaction mixture comprising the compound of Formula (IVb) and an organic solvent, further comprises a drying agent selected from the group consisting of molecular sieves, calcium chloride, magnesium sulfate, sodium sulfate, activated charcoal, or a combination thereof.

Embodiment A41 is the process of any of embodiments A33 to A40, wherein the reaction mixture comprising the compound of Formula (IVb) and an organic solvent is heated to a temperature from about 20° C. to about 100° C.

Embodiment A42 is the process of embodiment A41, wherein the reaction mixture comprising the compound of Formula (IVb) and an organic solvent is heated to a temperature from about 40° C. to about 80° C.

Embodiment A43 is the process of embodiment A42, the reaction mixture comprising the compound of Formula (IVb) and an organic solvent is heated to a temperature from about 50° C. to about 70° C.

Embodiment A44 is the process of any of embodiments A1 to A43, wherein heating the compound of Formula (IV) forms a product mixture comprising the compound of Formula (I) and the process further comprises filtering the product mixture to form a solids fraction and a filtrate comprising the compound of Formula (I).

Embodiment A45 is the process of embodiment A44, wherein the compound of Formula (I) is recovered from the product mixture filtrate, and purified by washing with solvent, by recrystallization, or by a chromatographic method.

Embodiment A46 is the process of embodiment A44, wherein the product mixture filtrate is washed with a solvent to form a slurry, and the product compound of Formula (I) is recovered from the slurry by filtration, the product having a purity of at least 95%.

Embodiment A47 is the process of embodiment A44, wherein the product mixture filtrate is passed through a silica column and the product compound of Formula (I) is recovered, the product having a purity of at least 95%.

Embodiment A48 is the process of any of embodiments A1 to A47, wherein the compound of Formula (I) is 1-[2-(9(Z)-octadecenoyloxy)ethyl]-2-(8(Z)-heptadecenyl)-3-(2-hydroxyethyl)imidazolinium chloride (DOTIM):

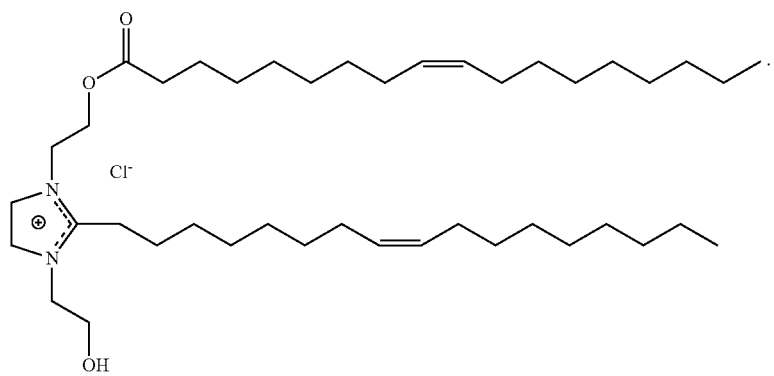

Embodiment B1 is a process for preparing a compound of Formula (I)

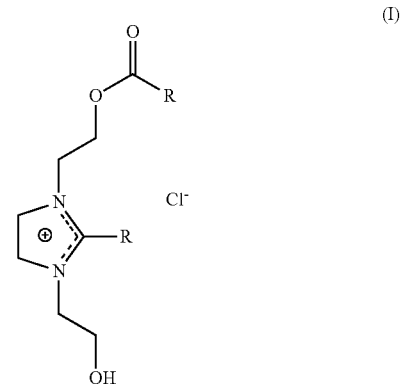

wherein R is a straight-chain, aliphatic, saturated or unsaturated hydrocarbyl group of 11 to 29 carbon atoms, the process comprising:

heating a compound of Formula (IV) in a reaction mixture comprising an organic solvent and a base to provide the compound of Formula (I)

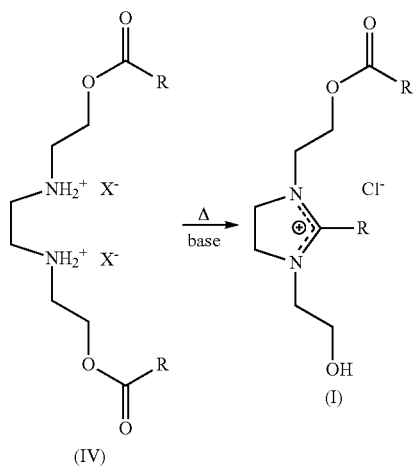

wherein R is as defined above for Formula (I) and X is Cl, Br, or I.

Embodiment B2 is the process of embodiment B1 further comprising washing a compound of Formula (IVa) wherein X is not Cl with an aqueous solution of sodium chloride to provide a compound of Formula (IVb), and the reaction mixture comprises a compound of Formula IV(b)

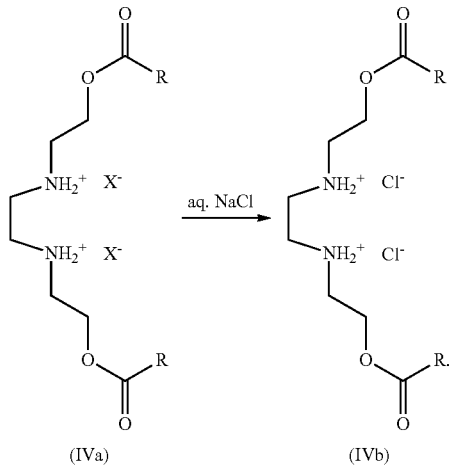

(IVa)    (IVb)

Embodiment B3 is the process of embodiment B1 or B2, wherein the base is a weak base.

Embodiment B4 is the process of any of embodiments B1 to B3, wherein the base is sodium bicarbonate, potassium bicarbonate, potassium dihydrogen phosphate, dipotassium hydrogen phosphate, a tertiary amine, or a mixture thereof.

When introducing elements of the present invention or the preferred embodiments(s) thereof, the articles "a", "an", "the" and "said" are intended to mean that there are one or more of the elements. The terms "comprising", "including" and "having" are intended to mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and provided herein shall be interpreted as illustrative and not in a limiting sense.

What is claimed is:

1. A process for preparing a compound of Formula (I)

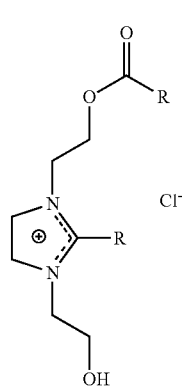

(I)

wherein R is a straight-chain, aliphatic, saturated or unsaturated hydrocarbyl group of 11 to 29 carbon atoms, the process comprising: reacting a compound of Formula (II) with a hydrogen halide (HX) to provide a compound of Formula (III), wherein X is Cl, Br, or I;

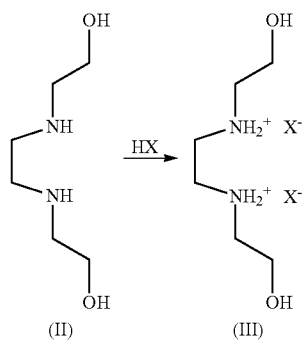

(II)    (III)

reacting the compound of Formula (III) with a carboxylic acid halide [RC(O)Y], wherein R is as defined above for formula (I) and wherein Y is selected from the group consisting of Cl, Br, F, and I, or a carboxylic acid anhydride [RC(O)OC(O)R$^2$], wherein R is as defined above for Formula (I) and R$^2$ is a straight-chain or branched, aliphatic, saturated or unsaturated hydrocarbyl group of 1 to 29 carbon atoms, to provide a compound of Formula (IV); and

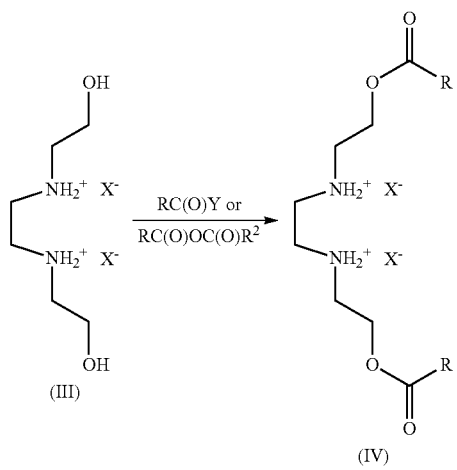

(III)    (IV)

heating the compound of Formula (IV) to provide a compound of Formula (I)

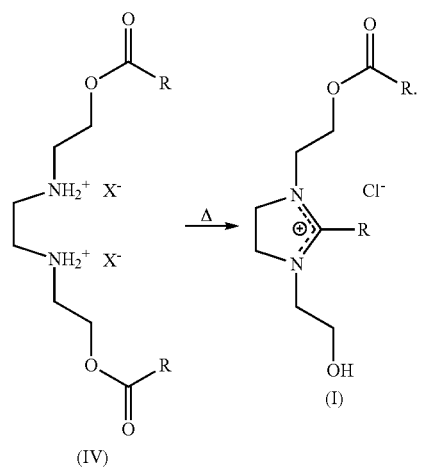

(IV)    (I)

2. The process of claim 1, wherein the compound of Formula (III) is reacted with the carboxylic acid halide [RC(O)Y], and X is not Cl and a compound of Formula (IVa) is provided, the process further comprising washing the compound of Formula (IVa) with an aqueous solution of sodium chloride to provide a compound of Formula (IVb)

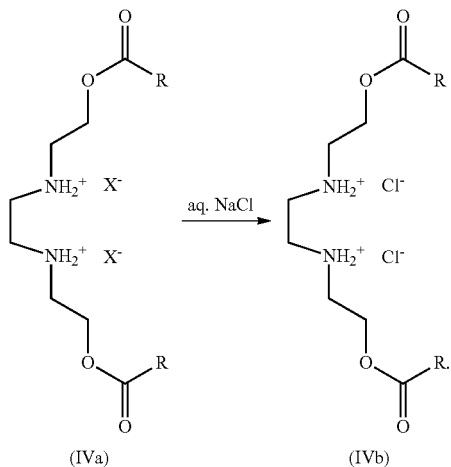

3. The process of claim 1, wherein the compound of Formula (III) is reacted with the carboxylic acid anhydride [RC(O)OC(O)R$^2$], or the carboxylic acid halide [RC(O)Y] and X=Cl and a compound of Formula (IVb) is provided

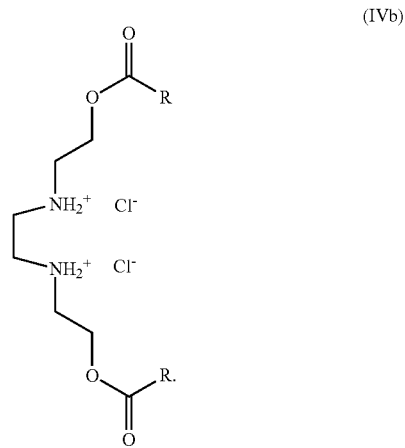

4. The process of claim 1, wherein the compound of Formula (III) is reacted with the carboxylic acid halide or the carboxylic acid anhydride in the absence of an acid catalyst.

5. The process of claim 1, wherein the compound of Formula (III) is reacted with the carboxylic acid halide or the carboxylic acid anhydride in the absence of an acid catalyst selected from the group consisting of p-toluene sulfonic acid, benzenesulfonic acid, sulfoacetic acid, a phosphorus acid, and phosphorus trichloride.

6. The process of claim 1, wherein the compound of Formula (II) is reacted with the hydrogen halide (HX) in a reaction mixture further comprising an organic solvent selected from the group consisting of $C_2$-$C_6$ carboxylic acids, $C_2$-$C_6$ nitriles, $C_1$-$C_6$ alcohols, $C_2$-$C_{10}$ ethers, $C_3$-$C_6$ alkyl acetates, $C_3$-$C_{10}$ ketones, $C_5$-$C_8$ aliphatic hydrocarbons, $C_1$-$C_6$ chlorinated hydrocarbons, $C_3$-$C_8$ alkyl carbonates, sulfolane, dimethyl sulfoxide, toluene, chlorobenzene and combinations thereof.

7. The process of claim 1, wherein the compound of Formula (II) is reacted with the hydrogen halide HX at a temperature from about 0° C. to about 60° C.

8. The process of claim 1, wherein R$^2$ is a $C_1$-$C_{10}$ straight-chain or branched aliphatic hydrocarbon.

9. The process of claim 1, wherein the compound of Formula (III) is reacted with the carboxylic acid halide [RC(O)Y], wherein R is a $C_{11}$-$C_{29}$ straight-chain, aliphatic, hydrocarbyl group, and Y is Cl or Br.

10. The process of claim 1, wherein the compound of Formula (III) is reacted with the carboxylic acid anhydride [RC(O)C(O)R$^2$], wherein R is a $C_{11}$-$C_{29}$ straight-chain saturated or unsaturated aliphatic hydrocarbyl group and R$^2$ is a $C_1$-$C_{10}$ straight-chain or branched aliphatic hydrocarbyl group.

11. The process of claim 1, wherein the compound of Formula (III) is reacted with the carboxylic acid anhydride [RC(O)OC(O)R$^2$], or the carboxylic acid halide [RC(O)Y] in a reaction mixture further comprising an organic solvent selected from the group consisting of $C_2$-$C_6$ nitriles, $C_2$-$C_{10}$ ethers, $C_3$-$C_6$ alkyl acetates, $C_3$-$C_{10}$ ketones, $C_5$-$C_8$ aliphatic hydrocarbons, $C_1$-$C_6$ chlorinated hydrocarbons, $C_3$-$C_8$ alkyl carbonates, sulfolane, dimethyl sulfoxide, toluene, chlorobenzene and combinations thereof.

12. The process of claim 1, wherein the compound of Formula (III) is reacted with the carboxylic acid anhydride or the carboxylic acid halide at a temperature from about 0° C. to about 120° C.

13. The process of claim 3, wherein a compound of the Formula (IV) wherein X is not Cl is contacted with an aqueous solution of sodium chloride to provide the compound of Formula (IVb).

14. The process of claim 13, wherein the compound of Formula (IV) wherein X is not Cl is contacted with the aqueous solution of sodium chloride in a reaction mixture further comprising an organic solvent selected from the group consisting of $C_2$-$C_6$ nitriles, $C_2$-$C_{10}$ ethers, $C_3$-$C_6$ alkyl acetates, $C_3$-$C_{10}$ ketones, $C_5$-$C_8$ aliphatic hydrocarbons, $C_1$-$C_6$ chlorinated hydrocarbons, toluene, chlorobenzene and combinations thereof.

15. The process of claim 14, wherein the compound of Formula (IV) wherein X is not Cl is contacted with an aqueous solution of sodium chloride at a temperature from about 0° C. to about 60° C.

16. The process of claim 2, wherein the compound of Formula (IVb) is heated in a reaction mixture comprising the compound of Formula (IVb) and an organic solvent selected from the group consisting of $C_2$-$C_6$ nitriles, $C_1$-$C_6$ alcohols, $C_2$-$C_{10}$ ethers, $C_3$-$C_6$ alkyl acetates, $C_3$-$C_{10}$ ketones, $C_5$-$C_8$ aliphatic hydrocarbons, $C_1$-$C_6$ chlorinated hydrocarbons, $C_3$-$C_8$ alkyl carbonates, sulfolane, dimethyl sulfoxide, toluene, chlorobenzene and combinations thereof.

17. The process of claim 16 wherein the reaction mixture comprising the compound of Formula (IVb) further comprises a weak base selected from the group consisting of sodium bicarbonate, potassium bicarbonate, potassium dihydrogen phosphate, dipotassium hydrogen phosphate, a tertiary amine, and a mixture thereof.

18. The process of claim 16, wherein the reaction mixture comprising the compound of Formula (IVb) and an organic solvent, further comprises a drying agent selected from the group consisting of molecular sieves, calcium chloride, magnesium sulfate, sodium sulfate, activated charcoal, and a combination thereof.

19. The process of claim 16, wherein the reaction mixture comprising the compound of Formula (IVb) and the organic solvent is heated to a temperature from about 20° C. to about 100° C.

20. The process of claim 1, wherein heating the compound of Formula (IV) forms a product mixture comprising the compound of Formula (I) and the process further comprises filtering the product mixture to form a solids fraction and a filtrate comprising the compound of Formula (I).

21. The process of claim 20, wherein the compound of Formula (I) is recovered from the product mixture filtrate, and purified by washing with solvent, by recrystallization, or by a chromatographic method.

22. The process of claim 1, wherein the compound of Formula (I) is 1-[2-(9(Z)-octadecenoyloxy)ethyl]-2-(8(Z)-heptadecenyl)-3-(2-hydroxyethyl)imidazolinium chloride (DOTIM):

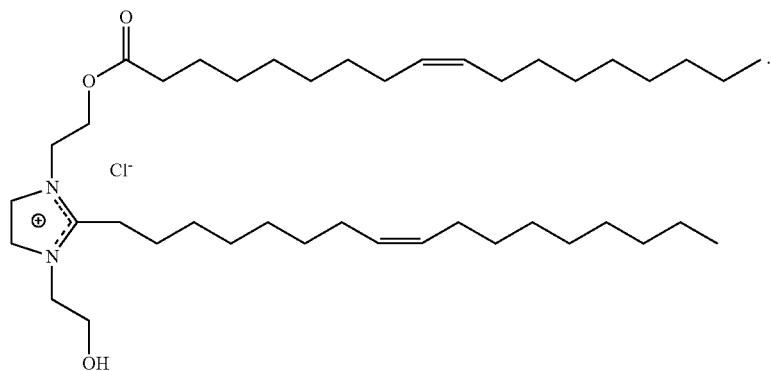

23. A process for preparing a compound of Formula (I)

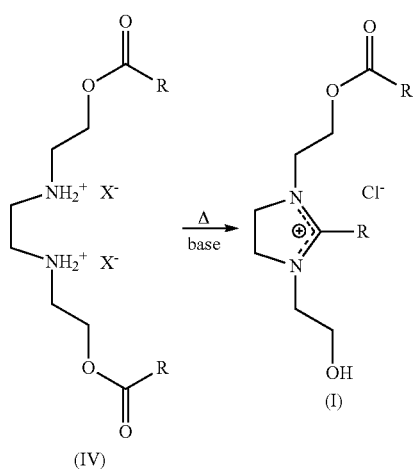

wherein R is a straight-chain, aliphatic, saturated or unsaturated hydrocarbyl group of 11 to 29 carbon atoms, the process comprising:

heating a compound of Formula (IV) in a reaction mixture comprising an organic solvent and a base to provide the compound of Formula (I)

wherein R is as defined above for Formula (I) and X is Cl, Br, or I.

24. The process of claim 23 further comprising washing a compound of Formula (IVa) wherein X is not Cl with an aqueous solution of sodium chloride to provide a compound of Formula (IVb), and the reaction mixture comprises a compound of Formula IV(b)

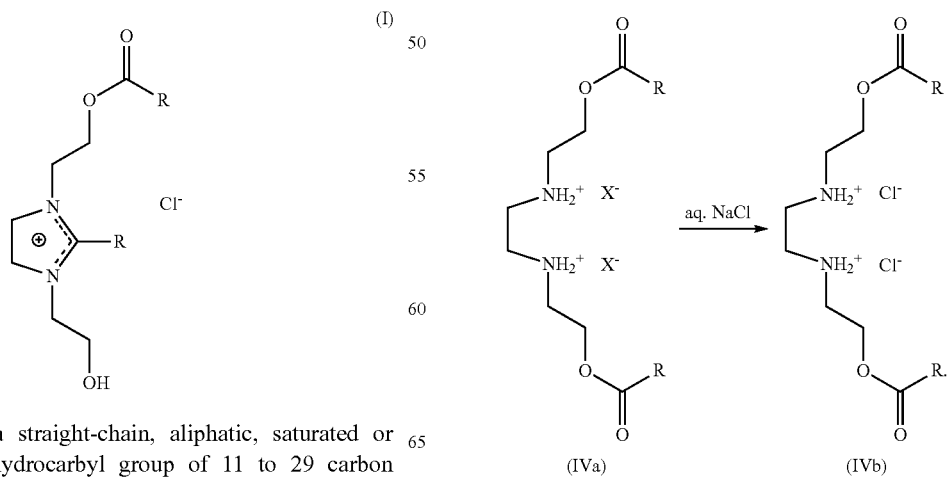

25. The process of claim 23, wherein the base is a weak base selected from sodium bicarbonate, potassium bicarbonate, potassium dihydrogen phosphate, dipotassium hydrogen phosphate, a tertiary amine, or a mixture thereof.

* * * * *